United States Patent
Soi et al.

(10) Patent No.: US 8,816,132 B2
(45) Date of Patent: *Aug. 26, 2014

(54) PROCESS OF PRODUCING POLYGLYCEROL FROM CRUDE GLYCEROL

(75) Inventors: Hoong Seng Soi, Kajang (MY); Zailan Abu Bakar, Kajang (MY); Nik Siti Mariam Nek Mat Din, Kajang (MY); Zainab Idris, Kajang (MY); Yeong Shoot Kian, Kajang (MY); Hazimah Abu Hassan, Kajang (MY); Salmiah Ahmad, Kajang (MY)

(73) Assignee: Malaysian Palm Oil Board (MPOB), Selangor Darul Ehsan (MY)

( * ) Notice: Subject to any disclaimer, the term of this patent is extended or adjusted under 35 U.S.C. 154(b) by 428 days.

This patent is subject to a terminal disclaimer.

(21) Appl. No.: 12/776,092

(22) Filed: May 7, 2010

(65) Prior Publication Data

US 2011/0118508 A1    May 19, 2011

(30) Foreign Application Priority Data

May 8, 2009    (MY) ............................. PI 20091872

(51) Int. Cl.
*C07C 41/01*    (2006.01)
*C08G 65/46*    (2006.01)
*C08G 65/34*    (2006.01)
*C07C 41/09*    (2006.01)

(52) U.S. Cl.
CPC ............... *C08G 65/34* (2013.01); *C08G 65/46* (2013.01); *C07C 41/09* (2013.01)
USPC .......................................... 568/619; 568/621

(58) Field of Classification Search
None
See application file for complete search history.

(56) References Cited

U.S. PATENT DOCUMENTS 3,356,738 A * 12/1967 Hauser et al. ................. 568/621
3,932,532 A *  1/1976 Hunter et al. ................. 568/613

FOREIGN PATENT DOCUMENTS

| EP | 0 518 765 A1 | 12/1992 |
| EP | 0518765 * | 12/1992 |
| EP | 0 719 752 A1 | 7/1996 |
| WO | 2004/065343 A2 | 8/2004 |
| WO | 2007-049950 A2 | 5/2007 |

OTHER PUBLICATIONS

Co-pending U.S. Appl. No. 12/821,294, filed Jun. 23, 2010.*
European Search Report, dated Nov. 15, 2010 for European Application No. 10162361.9.
U.S. Appl. No. 12/821,294, filed Jun. 23, 2010, Office Action dated Sep. 24, 2012.
U.S. Appl. No. 12/821,294, filed Jun. 23, 2010, Final Office Action dated May 2, 2013.
Soares et al., Soybean—Applications and Technology, Chapter 9—New Applications for Soybean Biodiesel Glycerol, pp. 151-172, 2011.

* cited by examiner

*Primary Examiner* — Rosalynd Keys
(74) *Attorney, Agent, or Firm* — Workman Nydegger

(57) ABSTRACT

The present invention relates to a process for accelerated preparation of polyglycerol from crude glycerol using microwave irradiation as the heat element in the presence of soap as the catalyst. The process includes the steps of (a) heating the crude glycerol that contain soap to an elevated temperature for a certain reaction time by using a microwave technology, (b) acidifying the crude polyglycerol with mineral acid at a specific temperature and centrifuging acidified crude product obtained from step (b) at a specific temperature for a certain duration of time.

15 Claims, No Drawings

PROCESS OF PRODUCING POLYGLYCEROL FROM CRUDE GLYCEROL

FIELD OF INVENTION

The present invention relates to a process for producing polyglycerol from crude glycerol.

BACKGROUND OF INVENTION

Polyglycerols are commonly prepared through thermal dehydration of glycerol, in which the polymerisation was carried out at atmospheric pressure and at an elevated temperature, which is about 230° C.-270° C. The process can be accomplished without the Use of catalyst but the yield of polyglycerol is considerably low.

Therefore, various catalysts have been introduced to aid in the formation of polyglycerol and the most commonly used catalysts are alkaline catalysts such as sodium or potassium hydroxide, alkaline carbonates such as potassium carbonate with aluminium oxide and alkaline earth metal hydroxide such as calcium hydroxide.

Acidic catalysts were also used in the thermal dehydration of glycerol such as mixtures of sulphuric acid and triacetin, hypophosphorus acid with sodium hydroxide and acidic zeolite. In addition, clay such as hydrotalcite was also used to catalyse thermal dehydration of glycerol.

Polyglycerol formation was also reported with either solketal, glycidol or glycerol carbonate as the reactants when reacted with hydrotalcite at elevated temperatures. In addition, glycidol, glycerol carbonate and solketal were polymerised using the fluoride salts of rubidium, caesium and potassium into polyglycerol. Furthermore, both linear and cyclic polyglycerols were reported as products of reaction between glycidol, glycerol carbonate and solketal with β-zeolites as catalysts.

A process to produce polyglycerol, which comprised reacting glycerol, diglycerol or higher polyglycerol with epichlorohydrin at 90° C. to 170° C. to produce a crude chlorohydrin/ ether mixture, followed by adding an amount of strong base at least substantially equivalent to the organically bound chlorine content of the chlorohydrin/ether mixture, and desalting the mixture and recovering the glycerol, diglycerol and higher polyglycerol fractions is also known in the art.

Allyl alcohol is another route in preparing polyglycerols. The process involved epoxidation of the allyl alcohol, in which glycidol would be formed and then followed by polymerisation of the glycidol. This was proven as another effective method to prepare polyglycerol.

Despite the fact that the background art in preparing polyglycerol is crowded and diverse, it is evident that the synthesis of polyglycerol and diglycerol from glycerol has several drawbacks. One of the drawbacks is the duration of reaction where most of the prior arts were reported to have a reaction time of minimum 5 hours to 72 hours, which would incur higher cost to the process. In addition, most of the prior arts disclosed that the composition of the final product (polyglycerol) still contains significant amount of glycerol that requires additional removal steps.

Another drawback of the prior arts is the use of high purity compounds such as glycerol, epiclorohydrin, glycidol, glycerol carbonate and solketal as the starting material in the preparation of polyglycerol. These chemical compounds are expensive and their cost makes up the bulk of the production cost of polyglycerol. Furthermore, most of the prior arts needed catalysts that were introduced to the reactants at certain point of the production process. The introduction of catalyst to the reactants also increases the production cost of polyglycerol.

Therefore, it is an objective of this invention to provide a process to produce polyglycerol that contains no residual glycerol in shorter time. Another objective of the invention is to use feedstock of lower purity that contains a suitable catalyst for the reaction. This invention would provide a process to produce polyglycerol with lower production cost.

SUMMARY OF THE INVENTION

Accordingly, the present invention provides a process for preparing polyglycerol from crude glycerol, the process includes the steps of (a) heating the crude glycerol that contain soap to an elevated temperature for a certain reaction time by using a microwave technology, (b) acidifying the crude polyglycerol with mineral acid at a specific temperature and (c) centrifuging acidified crude product obtained from step (b) at a specific temperature for a certain duration of time.

The present invention consists of several novel features and a combination of parts hereinafter fully described and illustrated in the accompanying description, it is being understood that various changes in the details may be made without departing from the scope of the invention or sacrificing any of the advantages of the present invention.

DETAILED DESCRIPTION OF THE PREFERRED EMBODIMENTS

The present invention relates to a process for producing polyglycerol from crude glycerol. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The present invention provides improvement to the current method of producing polyglycerols from glycerol. The improvement in this invention was made evident by the use of lower quality (cheaper) feedstock that contained suitable catalyst for the process. Preferably, the lower quality feedstock is crude glycerol derived from biodiesel plant. More specifically, the crude glycerol is the by-product from the production of methyl ester (biodiesel).

For this invention, it was preferred that the biodiesel derived crude glycerol's composition consisted of 60 to 80% glycerol, 10 to 25% methanol and 10 to 15% soap. More preferably, the crude glycerol contained 80 to 90% glycerol, 1 to 10% methanol and at least 10% soap. Most preferably, the crude glycerol contained only 85 to 90% glycerol and 10 to 15% soap. High content of methanol in the crude glycerol will increase the reaction time needed to fully convert the crude glycerol to polyglycerol and this will incur higher production cost.

It has been reported that polymerisation of glycerol to form polyglycerol can be carried out without the use of catalyst but the reaction suffered low yield of polyglycerol. Therefore, in this invention, a catalyst was used to increase the yield and selectivity of products. We discovered that fatty acid salts of alkaline metal (soap) gave good yield and selectivity in producing polyglycerol (especially those with degrees of polymerization, "n," ranging from 2 to 6) from glycerol. The soap may be, for example, a sodium or potassium salt of fatty acids comprising 8 to 22 carbon atoms in chain length (C8 to C22). We have disclosed earlier that the preferred crude glycerol contained 10 to 15% soap and this soap acts as a catalyst for the thermal dehydration reaction of glycerol to polyglycerol.

The soap in the crude glycerol was formed during the transesterification reaction between triglycerides and methanol that yield methyl ester (biodiesel), where the free fatty acid in the biodiesel feedstock reacted with the transesterification catalyst (sodium or potassium hydroxide or sodium methoxide) to yield the soap. In the biodiesel production process, the soap was removed together with the crude glycerol as by-product.

Examples of soap but not limited to this that could be found in the crude glycerol are sodium or potassium laurate, myristate, palmitate, stearate, oleate and linoleate. Preferably, the soap in the crude glycerol is sodium palmitate or sodium oleate. The preferred amount of soap in the crude glycerol is 0.1% to 15% and more preferably the amount of soap in the crude glycerol is not less than 10%. Most preferably, the amount soap in the crude glycerol is 10 to 15%. If the crude glycerol contains less than 10% soap, then the conversion of crude glycerol to polyglycerol will not achieve 100%.

The present invention also provides another improvement to the current method of producing polyglycerols from glycerol. The milestone improvement in this invention was made evident by the reaction time taken to completely convert crude glycerol to poyglycerol, which was in the range of 20 to 30 minute only, whereas the conventional method will take about 5 hours to 72 hours. This improvement results from the use of microwave irradiation, in which the crude glycerol was heated in a 900 W microwave oven in the presence of soap as the catalyst and was stirred with the aid from a magnetic stirrer. The preferred reaction time for microwave accelerated thermal dehydration of crude glycerol to polyglycerol is about 10 to 30 minute. More preferably, the reaction time is about 20 to 30 minute where the conversion of crude glycerol to polyglycerol could reach 95%. Most preferably the reaction time is 30 minute where the conversion of crude glycerol to polyglycerol was 100%.

For this invention, it was preferred that the temperature be in the range of 200° C. to 290° C., but more preferably in the range of 250° C. to 270° C. By employing temperatures in this range, it is possible to achieve good conversion with minimal side product while still obtaining acceptable reaction rates. The most preferred reaction temperature was 270° C. as the conversion of crude glycerol to polyglycerol was 100%. It is particularly preferred aspect of the invention, that the process be conducted at atmospheric pressure and by such operation the use of costly high-pressure equipment is avoided.

Crude polyglycerols prepared from crude glycerol still contained soap that will cause the product to become solid. The soap in the product could be removed through acidification of the crude product with phosphoric acid or any other mineral acids such as sulphuric, hydrochloric and nitric acid. The amount of the mineral acid used for acidifying the crude product was in the range of 1 to 3% (w/w). The final pH of the acidified product was in the range of 4 to 6, preferably in the range of 4 to 5.

The acidified crude product was then subjected to centrifugation. The acidified crude product was heated to 60-80° C. before the centrifugation process was started. The acidified crude product was centrifuged for at least 30 minute at 1500 to 2000 rpm. The centrifugal force was able to separate the fatty acid and salt from the product. The acidified crude product was separated into three layers after the centrifuge process. The top layer, was the fatty acid layer while the middle layer, was the purified polyglycerol. The bottom layer consists of salt and absorbed product.

The crude and purified polyglycerol samples were analyzed with High Performance Liquid Chromatography (HPLC) and the compositions of glycerol oligomers in each polyglycerol samples were determined. The HPLC system is equipped with an Evaporative Light Scattering Detector (ELSD). The samples analysis was achieved with a 25 cm×4.6 mm ID column prepacked with 10 μm Hypersil NH$_2$ amino at 30° C. An elution with acetonitrile (85%) and water (15%) was carried out at a flow rate of 1 ml/minute. The chromatographs were analyzed using software installed in the instrument to yield peak area and retention time. The samples were dissolved in water (2% w/v) and 20 μl of solution was injected by automatic loop injector.

Based on HPLC analysis results, the conversion of crude glycerol to polyglycerol reached 100% when the crude glycerol that contained 12% soap was subjected to microwave irradiation for 30 minutes at 270° C. The following is the typical composition of glycerol oligomers in the purified polyglycerol as analysed by HPLC:

Composition of Glycerol Oligomers
0%-3.5% of unreacted glycerol
52%-61% of diglycerol
25%-31% of triglycerol
11%-16% of tetraglycerol
0%-1% of higher polyglycerol According to the HPLC chromatogram, there is little or no evidence of cyclic diglycerol or polyglycerol found in the crude polyglycerol as it was compared to standard oligomers of glycerol. Therefore, the process can be claimed to be selective for producing linear diglycerol and polyglycerol from glycerol.

For comparison purpose, the same crude glycerol that contained 10% soap was heated to 270° C. and held at this temperature for 6 hours by using conventional heating in order to confirm the advantage of using microwave irradiation as the heat element, where the reaction time was greatly reduced to minutes as opposed to hours by using conventional heating. The analysis result showed that 90% conversion of crude glycerol to polyglycerol could only be achieved after 3 hours of reaction by using conventional heating method.

For comparison purpose, 10% sodium oleate (soap) was added into pure glycerol and the mixture was subjected to conventional heating and microwave heating at 270° C. for 6 hours and 30 minute respectively. HPLC analysis showed that 90% of pure glycerol could be converted to polyglycerol after 3 hours of reaction by conventional heating. For the reaction conducted with microwave heating, 100% of the pure glycerol was converted to polyglycerol after 30 minute of reaction. Therefore, this has proven that 10% soap was sufficient to convert 100% of glycerol to polyglycerol and microwave heating could reduce the reaction time from hours to 30 minute.

The following examples demonstrate the invention and facilitate its understanding

EXAMPLE 1

Biodiesel derived crude glycerol (100 g) that contained 80% glycerol, 12% soap and 6% methanol was charged into a 250 ml round bottom flask. The round bottom flask was then placed in the 900 W microwave oven cavity. Then, the microwave oven was programmed to raise the temperature from ambient to 270° C. in 3 minute and this temperature was maintained for another 27 minute, after which the cooling process was started to mark the end of reaction. The total reaction time was 30 minute. The crude polyglycerol was then subjected to High Performance Liquid Chromatography (HPLC) and the compositions of crude glycerol are shown as below. The yield of crude polyglycerol was 86% and the conversion percentage of crude glycerol to polyglycerol was 100%.
Composition of Glycerol Oligomers in Crude Polyglycerol
16% of soap
50% of diglycerol
22% of triglycerol
12% of tetraglycerol

EXAMPLE 2

The crude polyglycerol from Example 1 was subjected to a process to remove the soap in the crude product. The crude product was heated to 90° C. while stirring it with a magnetic stirrer and the acidification of the crude product was monitored by pH value. The initial pH of the crude product was about 9 and phosphoric acid was added drop-wise to the crude glycerol until the pH of the crude glycerol reached about 4. The acidified crude product was stirred for another 30 minute before transferring the acidified product to a centrifuge instrument. Under acidic condition, the soap was hydrolyzed to yield fatty acid and the sodium ion ($Na^+$) formed salt (sodium phosphate) with phosphoric acid. The centrifuge instrument was set to 60° C. and the acidified crude product was centrifuged for 30 minute at 1600 rpm. The acidified product was separated into 3 layers, in which the middle layer was the purified polyglycerol. The purified polyglycerol was then subjected to HPLC analysis and the compositions of each oligomers of glycerol are shown as below.
Composition of Glycerol Oligomers in Purified Polyglycerol
60% of diglycerol
26% of triglycerol
14% of tetraglycerol

EXAMPLE 3

The experiment in Example 1 was repeated with crude glycerol that contained 70% glycerol, 10% soap and 20% methanol. The crude product was subjected to the same purification process as described in Example 2. The following are the composition of the purified polyglycerol. The yield of crude polyglycerol was 69% and the conversion percentage of crude glycerol to polyglycerol was 100%.
Composition of Glycerol Oligomers in Purified Polyglycerol
57% of diglycerol
27% of triglycerol
16% of tetraglycerol

EXAMPLE 4

Biodiesel derived crude glycerol (100 g) that contained 80% glycerol, 12% soap and 6% methanol was charged into a three-necked 250 ml round bottom flask. The round bottom flask was connected to a condenser to collect any distillate. The content of the round bottom flask was heated to 270° C. for 3 hours by using conventional heating. The crude product was analysed by HPLC and the following are the composition of the crude product. The conversion percentage of crude glycerol to polyglycerol was about 90% after 3 hours of reaction.
Composition of Glycerol Oligomers in Crude Polyglycerol
10% of glycerol
30% of diglycerol
40% of triglycerol
20% of tetraglycerol

EXAMPLE 5

The experiment in Example 1 was repeated with pure glycerol that contained 10% of sodium oleate as the catalyst. The crude product was analysed by HPLC and the following are the composition of the crude product. The yield of crude polyglycerol was 89% and the conversion percentage of crude glycerol to polyglycerol was 100%.
Composition of Glycerol Oligomers in Crude Polyglycerol
65% of diglycerol
35% of triglycerol

EXAMPLE 6

The experiment in Example 4 was repeated with pure glycerol that contained 10% sodium oleate as the catalyst. The content of the round bottom flask was heated to 270° C. for 3 hours by using conventional heating. The crude product was analysed by HPLC and the following are the composition of the crude product. The conversion percentage of pure glycerol to polyglycerol was about 90% after 3 hours of reaction.
Composition of Glycerol Oligomers in Crude Polyglycerol
10% of glycerol
32% of diglycerol
28% of triglycerol
30% of tetraglycerol

The invention claimed is:
1. A process for preparing polyglycerol from crude glycerol, the process including the steps of:
   (a) heating the crude glycerol that contains about 60 to 90% glycerol and 10 to 15% by weight soap that is a salt of a fatty acid having from 8 to 22 carbon atoms to an elevated temperature from about 250° C. to about 270° C. for a reaction time from about 20 minutes to about 30 minutes by using a microwave technology, such that 95 to 100% of the crude glycerol is converted to linear polyglycerol(s) with no cyclic polyglycerol formation;
   (b) acidifying the crude polyglycerol product with mineral acid to hydrolyze the soap to yield a fatty acid and a salt of the mineral acid; and
   (c) centrifuging acidified crude product obtained from step (b) at 60-80° C., a centrifugal force of the centrifuging separating (1) the fatty acid and (2) the salt of the mineral acid from (3) the polyglycerol product, the acidified crude product separating into three layers including a layer of the fatty acid, a layer of the purified polyglycerol, and a layer of the salt of the mineral acid after centrifuging.
2. A process according to claim 1 where the crude glycerol is a by-product from the transesterification process of triglycerides with alcohol.
3. A process according to claim 1 where the methanol content of the crude glycerol is about 5 to 20%.
4. A process according to claim 1 where the soap is sodium or potassium salt of fatty acids comprising 8 to 22 carbon atoms in a chain length (C8 to C22).
5. A process according to claim 1 where the heat source is microwave irradiation generated by a microwave instrument.
6. A process according to claim 1 where the reaction is conducted at atmospheric pressure.
7. A process according to claim 1 where the crude polyglycerol is acidified by a mineral acid selected from the group consisting of phosphoric acid, sulphuric acid and nitric acid.
8. A process according to claim 1 where the crude polyglycerol is acidified by mineral acid to pH 4-6.

9. A process according to claim 1 where the crude polyglycerol is acidified at 90° C.

10. A process according to claim 1 where the acidified crude polyglycerol is centrifuged at 60° C.

11. A process according to claim 1 where the acidified crude polyglycerol is centrifuged for at least 30 minutes.

12. A process according to claim 1 where the acidified crude polyglycerol is centrifuged at 1500 to 2000 rpm.

13. A process according to claim 1 where the degree of polymerisation of crude polyglycerol varies from n =2 to 6.

14. A process for preparing polyglycerol comprising the steps of:
   a. applying microwave radiation to a feedstock comprising crude glycerol including about 60% to about 90% glycerol and that contains about 10 to 15% by weight soap that is a salt of a fatty acid having from 8 to 22 carbon atoms such that the feedstock is heated to an elevated temperature from about 250° C. to about 270° C. and held there for a reaction time from about 20 minutes to about 30 minutes until about 95% to about 100% of the glycerol has been selectively converted to linear polyglycerol(s) with substantially no cyclic polyglycerol formation;
   b. adding a mineral acid to the feedstock that has been processed in accordance with step (a) such that the final pH is about 4 to about 6, addition of the mineral acid hydrolyzing the soap to yield a fatty acid and a salt of the mineral acid; and
   c. centrifuging the feedstock that has been processed in accordance with step (b), a centrifugal force of the centrifuging separating (1) the fatty acid and (2) the salt of the mineral acid from (3) the polyglycerol product, the acidified crude product separating into three layers including a layer of the fatty acid, a layer of the purified polyglycerol, and a layer of the salt of the mineral acid after centrifuging.

15. A process for preparing polyglycerol comprising the steps of:
   a. applying microwave radiation to a feedstock comprising crude glycerol including about 60% to about 90% glycerol and about 10 to 15% by weight soap that is a salt of a fatty acid, the salt of the fatty acid being selected from the group consisting of sodium laurate, sodium myristate, sodium palmitate, sodium stearate, sodium oleate, sodium linoleate, potassium laurate, potassium myristate, potassium palmitate, potassium stearate, potassium oleate, and potassium linoleate such that the feedstock is heated to at least around about 250° C. to about 270° C. for at least about 30 minutes such that 100% of the crude glycerol is converted to linear polyglycerol(s) with no cyclic polyglycerol formation;
   b. adding a mineral acid to the feedstock that has been processed in accordance with step (a) until the feedstock that has been processed in accordance with step (a) has a pH of about 4 to about 6, addition of the mineral acid hydrolyzing the soap to yield a fatty acid and a salt of the mineral acid;
   c. centrifuging the feedstock that has been processed in accordance with step (b), a centrifugal force of the centrifuging separating (1) the fatty acid and (2) the salt of the mineral acid from (3) the polyglycerol product, the acidified crude product separating into three layers including a layer of the fatty acid, a layer of the purified polyglycerol, and a layer of the salt of the mineral acid after centrifuging.

* * * * *

UNITED STATES PATENT AND TRADEMARK OFFICE
CERTIFICATE OF CORRECTION

| | | Page 1 of 1 |
|---|---|---|
| PATENT NO. | : 8,816,132 B2 | |
| APPLICATION NO. | : 12/776092 | |
| DATED | : August 26, 2014 | |
| INVENTOR(S) | : Soi et al. | |

It is certified that error appears in the above-identified patent and that said Letters Patent is hereby corrected as shown below:

In the Specification

Column 3
Line 12, change "the amount soap" to --the amount of soap--

Signed and Sealed this
Seventh Day of July, 2015

Michelle K. Lee
*Director of the United States Patent and Trademark Office*